US005532379A

United States Patent [19]

Fujimoto

[11] Patent Number: 5,532,379
[45] Date of Patent: Jul. 2, 1996

[54] BIOTIN CONTAINING HETEROBIFUNCTIONAL CLEAVABLE COMPOUNDS

[75] Inventor: Edward K. Fujimoto, Rockford, Ill.

[73] Assignee: Pierce Chemical Company, Rockford, Ill.

[21] Appl. No.: 435,206

[22] Filed: May 5, 1995

[51] Int. Cl.[6] .................................................. C07D 235/02
[52] U.S. Cl. .......................................................... 548/304.1
[58] Field of Search ................................................ 548/304.1

[56] References Cited

PUBLICATIONS

Jacobson et al. Life Sciences, vol. 56, No. 11/12 Feb. 1995 p. 823–830.
Bioconjugate Chemistry Nov./Dec. 1994, vol. 5 No. 6. (Back cover).

*Primary Examiner*—Johann Richter
*Assistant Examiner*—Laura L. Stockton

[57] ABSTRACT

Trifunctional cross-linking compounds are disclosed. The compounds contain the biotin moiety, the NHS active ester, and a photoactivatable aryl azide. The presence of a disulfide bond in association with either the ester or azide permits the compound to be cleaved.

12 Claims, No Drawings

BIOTIN CONTAINING HETEROBIFUNCTIONAL CLEAVABLE COMPOUNDS

FIELD OF INVENTION

The present invention relates to new chemical compounds and, more particularly, to novel cross-linking reagents which have the biotin moiety covalently attached to a heterobifunctional reagent. The compounds of the present invention are cleavable and generally useful in those bioanalytical applications utilizing biotin, and particularly the avidin-biotin complex.

BACKGROUND OF INVENTION

In several reviews, Wilchek and Bayer have described many biotin containing reagents which have enhanced the versatility and utility of the avidin-biotin complex in studying biological interactions and accomplishing separations. *Methods in Enzymology*, Vol. 184[13], pp. 123–138, titled "Biotin-Containing Reagents" and *Analytical Biochemistry*, Vol. 171, pp. 1–32 (1988), titled *The Avidin-Biotin Complex in Bioanalytical Applications*. As observed in the first of these reviews, such reagents can be used for biotin labeling of a variety of sites (e.g., amino, thiols, imidazoles and phenols) on targets, binders and/or probes. The review also states that photoreactive reagents for indiscriminate labeling have been described. Wedelund, et al. describe a trifunctional biotin reagent containing the photo-reactive phenyl azide moiety for photoaffinity labeling. *Biol. Chem. Hoppe-Seyler*, Vol. 370 pp. 251–158 (March 1989). A reagent for covalently attaching biotin to proteins via a cleavable connector arm has also been described. Mouton, et al., *Archives of Biochemistry and Biophysics*, Vol. 218, No. 1, pp. 101–108 (1982).

SUMMARY OF THE INVENTION

The present invention provides new compounds, represented by the formula:

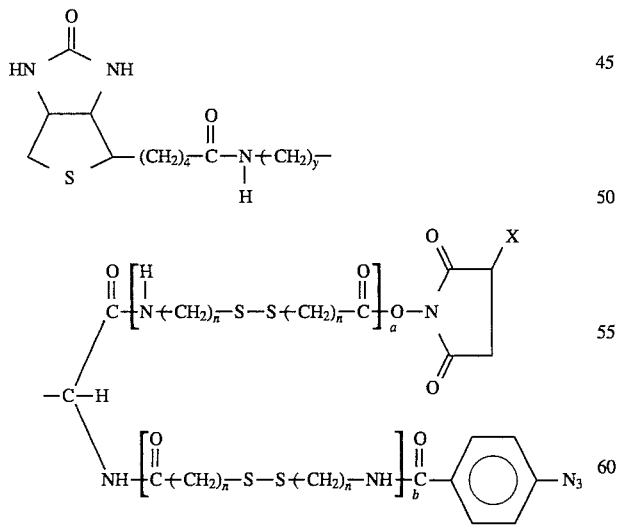

wherein a and b are zero or one, but are different, x is H or $SO_3$ Na, n is an integer of 1 to 10, each n being the same or different, and y is an integer of 1 to 10. Preferably, each n is 2 and y is 4.

As shown, the compounds are trifunctional in containing the biotin moiety, the N-hydroxysuccinimido active ester (NHS), and the photoactivatable aryl azide, each of these moieties being a branch of the central trigonal CH group. They are soluble in dimethyl sulfoxide (DMSO), dimethyl formamide (DMF), and methanol and, when x is the Sulfo-group, have some water solubility due to the Sulfo-NHS ester moiety. The presence of the disulfide bond permits cleavage (by, e.g., dithiothreitol or beta-mercaptoethanol) which can then provide a biotin label attached to a protein by photoactivation through the aryl azide moiety or through the NHS ester.

Thus, the novel compounds provide an investigator with many options which may not be available with a single bifunctional reagent, cleavable or not. For example, the compounds provide the ability to biotinylate substances which may not be easily biotinylated by other means, or the creation of unique affinity matrices with ligands which may not be easily obtained by conventional means.

DESCRIPTION OF PREFERRED EMBODIMENTS

One preferred compound of the present invention is the compound wherein a is one and b is zero, x is $SO_3$ Na, each n is 2, and y is 4. This compound is Sulfosuccinimidyl-2[6-biotinamido)-2-(p-azidobenzamido)-hexanoamido]ethyl-1,3'-dithiopropionate and herein termed Sulfo-SBED. A use of this compound has been reported. *Life Sciences*, Vol. 56, No. 11/12 pp. 823–830, 1995.

In a typical use, this compound, as well as the others described herein, can be reacted first with the primary amino groups of a protein or other molecule through the NHS-ester moiety of the compound under subdued light to protect the aryl azide moiety from light. The reaction can be accomplished in an aqueous medium at room temperature. The coupling reaction should be accomplished using buffers that do not contain primary amines or sulfhydryls. After removal of unreacted and hydrolyzed Sulfo-SBED by, for example, gel filtration or dialysis, the modified protein can be coupled by photoactivation to the second substance. The resulting biotinylated cross-linked substance can find use in biotin separation techniques and immuno assay development.

In another use, the cross-linked substance can first be captured on an affinity support with specificity toward biotin, e.g., immobilized streptavidn. Subsequent reduction (cleavage) of the disulfide bond of the cross-linked complex results in the preparation of an affinity matrix. The ligand of this newly created affinity matrix is the compound which was coupled to the protein via the aryl azide moiety of the Sulfo-SBED. Alternatively, cleavage can be accomplished before attachment to the support.

The following Examples I–IV illustrates the preparation of Sulfo-SBED. All steps were carried out in subdued light.

EXAMPLE I

Preparation of
2-(p-Azidobenzamido)-6-(biotinamido)hexanoic acid

In a 1 L flask is placed biocytin (4.85 g–13.02 mm), sodium bicarbonate (4.27 g–50.82 mm), and 173 ml deionized water. The mixture is stirred at room temperature for ~¾ hr. to give an essentially clear and colorless mixture. Commercially available N-hydroxysuccinimdyl 4-azidobenzoate (HSAB,) (3.30 g–12.68 mm) is added as a solid. 163 ml of dioxane is added, the system sealed with a bubbler and stirred overnight at room temperature for ~21 hrs. The reaction mixture is rotary evaporated in vacuo using water aspirator as vacuum source and a water bath at ≦41 C. to isolate damp residue.

Thereafter, 485 ml deionized water is added, the system sealed and stirred at room temperature for ~½hr. to give very slightly cloudy mixture. It is further stirred at 0–4 C. for ~18 hrs. and suction filtered and washed with 55 ml deionized water. The filtrate is diluted further with the addition of 623 ml deionized water. The diluted filtrate is acidified with 6.8 ml of hydrochloric acid (12N) delivered dropwise over a period of ~4–5 min. using a disposable pipet to give a slurry which is slurried at room temperature for ~12 min. The slurry is then filtered, washed with 1.39 L deionized water and air dried on Buchner funnel for ~½–1 hr. The damp product is transferred to a beaker and then dried in vacuum desiccator over potassium hydroxide pellets to a weight of ~5.64 g.

EXAMPLE II

Preparation of Succinimidyl 2-(p-azidobenzamido)-6-(biotinamido) hexanoate

In a 215 ml flask is placed the product of Example I (5.64 g 10.90 mm), NHS(1.37 g–11.90 mm), and 86 ml DMF. The mixture is stirred under a nitrogen atmosphere at room temperature for about 15 min. to give an essentially clear mixture with a very pale yellow cast. It is then cooled in a dry acetone bath to give a slurry and then a mixture of N, N' dicyclohexylcarbodiimide (DCC) (2.55 g–12.36 mm) in 6 ml DMF is added over a period of about 3 min. using a disposable pipet. It is then washed with 10 ml DMF. The resulting lighter slurry is stirred in dry ice acetone for an additional 3 min. and then at room temperature for about 15 min. to give a heavier slurry.

The system is then sealed and further slurried in a cold box at 0–4 C. for an additional 2 days. It is then allowed to stand at room temperature for about 1 hr. under a nitrogen atmosphere to reduce condensation during the following filtration. Via vacuum adapter with Buchner the slurry is filtered and washed with 13 ml DMF. The N,N'-dicyclohexylurea (DCU) residue is discarded. The filtrate is evaporated in vacuo with bath temperature reaching 44 C. To the oily residue is added 378 ml isopropyl alcohol (IPA) and the mixture stirred at atmospheric pressure for about ½hr. in a water bath at 75–77 C.

The liquid mixture is filtered using 79 ml IPA as a wash and then a slurry formed by the addition of 614 ml of hexane under nitrogen. The system is sealed and stirred overnight. The slurry is then allowed to settle and then filtered and washed with 1 L hexane. The residue is dried on a Buchner funnel with slow nitrogen sweep for about ¾hr. and then transferred to a beaker. It is further dried in a vacuum oven (about 28" Hg) at room temperature.

EXAMPLE III

Preparation of 2-[6(biotinamido)-2-(p-azidobenzamido)hexanoamido]ethyl-1,3'-dithiopropionate acid (BED ACID)

In a 1 L flask is placed the known compound, 2-aminoethyl-2'carboxyethyl disulfide (1.83 g–10.09 mm), sodium bicarbonate (2.27 g–27.02 mm), and 35 ml deionized water. A magnetic stir bar is added and the mixture stirred at room temperature for ~¾hr. to give an essentially clear and colorless mixture. Succinimidyl 2-(p-azidobenzamido)-6-(biotinamido)hexanoate (5.15 g–8.379 mm), prepared as in Example II, is added as a solid. 68 ml of dioxane is added and system sealed and stirred at room temperature for ~21 hrs.

The mixture is evaporated in vacuo using a water aspirator as vacuum source and water bath at ≦40 C. to isolate a damp residue. About 441 ml water is added and the mixture sealed and then stirred at room temperature for ~1.5 hr. then stirred further at ~0–4 C. for two days to give a very light slurry. The slurry is filtered and washed with 74 ml deionized water. The slightly hazy filtrate is diluted with the addition of 258 ml water to give clear filtrate with very pale yellow cast. The filtrate is stirred and acidified with 4.1 ml of hydrochloric acid (12N) delivered dropwise over a period of ~4–5 min. using a disposable pipet to give slurry which is slurried further at room temperature for ~¾–1 hr. The slurry is filtered to isolate product which is washed with 662 ml deionized water and air dried for ~½–1 hr. The damp product is transferred to crystallizing dish and then dried in a vacuum desiccator over potassium hydroxide pellets to a constant weight and then transferred to an amber bottle.

EXAMPLE IV

Preparation of Sulfo-SBED

In a 50 ml suction flask was placed 2-[6-(biotinamido)-2-(p-azidobenzamido)hexanoamido-ethyl-1,3'dithiopropionic acid (BED ACID) (1.5000 g–2.203 mm), Prepared as in Example III, Sulfo-NHS (0.5074 g–2.337 mm), and 33.9 ml DMF. A magnetic stir bar and a nitrogen atmosphere were applied, and the mixture stirred at room temperature for ~15 min. to give a light slurry. The mixture was then cooled in a dry ice acetone bath and then a mixture of DCC (0.5163 g–2.502 mm) in 1.03 g or 1.1 ml DMF was added using a disposable pipet. 3.3 ml DMF was used as wash. Addition and wash time was ~5min. Stirring in a dry ice acetone bath for ~3 min. and then at room temperature for ~15 min. was accomplished and the system, while still under nitrogen, sealed then slurried further in a cold box at 0° C. for an additional five days.

After removal from the cold box, the mixture was allowed to stand at room temperature for ~2 hours under a nitrogen atmosphere. It was then suction filtered and the filtrate collected in a tared 1 L pear shaped flask. The residue was washed with 5.6 ml DMF and residual by-product DCU discarded.

The clear pale straw yellow filtrate was rotary evaporated using a vacuum pump pulling ≦1–2 mm Hg vacuum and with bath temperature reaching 40° C. The final oily solid weighed 3.0 g. 500 ml of methylene chloride and magnetic stir bar were added and the system sealed with a rubber stopper and then stirred at room temperature for 3 days to give a free flowing slurry which was allowed to settle overnight.

The slurry was filtered and the off-white residue washed with 1000 ml methylene chloride and 500 ml hexane. The product was collected on 5.5cm filter paper (Whatman 1).

The residue was briefly dried on a Buchner with slow nitrogen sweep for ~1 hr and then placed in a 30cc wide mouth amber bottle. The residue weighed 2,194 g. It was then dried further in a vacuum oven (~28" Hg) over potassium hydroxide pellets at room temperature to a weight of 1,796 g. The yield was 92.6%. Elemental analysis yielded the following: H,5.12; C,43.83; N,13.45; 0,20.74; S,14.44; Na,2.54. Calc'd: H,4.81; C,43.68; N,14.33; 0,20.00; S,14.57; Na,2.61.

If the non-sulfonated compound, SBED, is desired, then simply NHS rather than Sulfo-NHS is used in Example IV, and the isolation technique modified to account for the fact that the resultant product has diminished water solubility.

The following Example illustrates the use of Sulfo-SBED in coupling with Trypsin and Soybean Trypsin Inhibitor. Again, until photoactivation, all steps are carried out in subdued light.

EXAMPLE V

In a microcentrifuge tube, 5 mg of soybean trypsin inhibitor (STI) are dissolved in 0.5 ml of 0.1 M PBS buffer, pH 7.2; 11 microliters of a freshly prepared solution of Sulf-SBED in DMSO (1.12 mg Sulfo-SBED in 25 microliters of DMSO) is then added thereto and the solution incubated, at room temperature for 30 minutes (or on ice for 2 hours). Any precipitate formed (hydrolyzed Sulfo-SBED) can be removed by brief centrifuging and any balance of unreacted Sulfo-SBED removed by application of the solution to a desalting column(Product No. 43230—all Product Nos. herein being those of Pierce Chemical Company, of Rockford, Ill.) equilibrated with "BupH" PBS buffer (Product No. 28372). While still in the dark, 500 microliter fractions are eluted with PBS and collected; the biotinylated STI being eluted in the void volume. To check for protein, 10 microliters of each fraction are mixed with 200 microliters of BCA Protein Assay Reagent (Product No. 23225). After incubation at room temperature, those early fractions having a purple color denoting protein are pooled.

To conjugate biotinylated STI with trypsin, 5 mg of TPCK trypsin (Product No. 20233) dissolved in 0.5 ml PBS are mixed with the biotinylated STI obtained as above. The solution is incubated for about 3.5 minutes at room temperature and then photolyzed with a long wave UV lamp (365 nm) at a distance of 5 cm for 15 minutes. Desalting is accomplished in ambient light with a 10 ml desalting column (Product No. 43233) equilibrated with PBS, and 1 ml fractions collected, with those containing protein being pooled as above described.

Cleavage of the disulfide bond to yield just the biotinylated typsin can be achieved by incubating the pooled fractions with 50 mM DTT (Product No. 20290) or 100 mM beta-mercaptoethanol (Product No. 35601).

The following Examples illustrate the preparation of the compound, Sulfosuccinimidyl 2-[2-(p-azidobenzamido)ethyl-1,3'—dithiopropionamido]-6-(biotinamido) hexanoate. This compound, termed Sulfo-SABH, is represented by the foregoing formula where a is zero, b is one, x is $SO_3$ Na, each n is 2, and y is 4.

EXAMPLE VI

Preparation of 2(p-azidobenzamido)ethyl,1,3'-dithiopropionic acid (AEP).

In a 1L flask is placed the known compound 2-aminoethyl-2'carboxyethyl disulfide (2.48 g–13.68 mm), sodium bicarbonate (3.09 g–36.78 mm), and 47 ml deionized water. The mixture is stirred to give a clear mixture. The previously described HSAB (2.96 g–11.38 mm) is added as a solid. 92 ml of dioxane is added, the system sealed with a bubbler and stirred overnight at room temperature. The reaction mixture is rotary evaporated in vacuo using water aspirator a vacuum source and a water bath at ~43 C. to isolate damp solid.

Thereafter, 600 ml deionized water is added, the system sealed and stirred at room temperature for four hours. It is further stirred at ~0 C. for ~19 hrs. and suction filtered and washed with 100 ml deionized water. The filtrate is diluted further with the addition of 350 ml deionized water. The diluted filtrated is acidified with 5.6 ml of hydrochloric acid (12 N) delivered dropwise over a period of 2 min. using a disposable pipet to give a slurry which is slurried at room temperature for 15 min. The slurry is then filtered, washed with 1L deionized water and air dried on Buchner funnel for ~1 hr. The damp product is transferred to a beaker and then dried in vacuum desiccator over potassium hydroxide pellets to a weight of ~3.37 g.

EXAMPLE VII

Preparation of Succinimdyl 2(p-azidobenzamido(ethyl-1,3'-dithiopropionate) (SAEP).

AEP (1.6322 g–5.00 mm), prepared per Example VI, is reacted with NHS (0.5754 g–5.00 mm) and DCC (1.0703 g–5.19 mm) in 20 ml of the reaction solvent DMF per the analogous reaction type described in Example II. The crude product isolated after removal of the DCU by-product and the solvent DMF is further purified by crystallization from a solvent mixture of methylene chloride and hexane. The product isolated after filtration is dried in a vacuum oven (~28 Hg) at room temperature.

EXAMPLE VIII

Preparation of Sulfo-SABH

The general procedure of Example I is used except that SAEP, prepared per Example VII, is used instead of HSAB yielding a product termed ABH Acid. Then, the general procedure of Example IV is employed substituting ABH Acid for the BED Acid to yield the product, Sulfo-SABH.

What is claimed is:

1. A compound having the structure

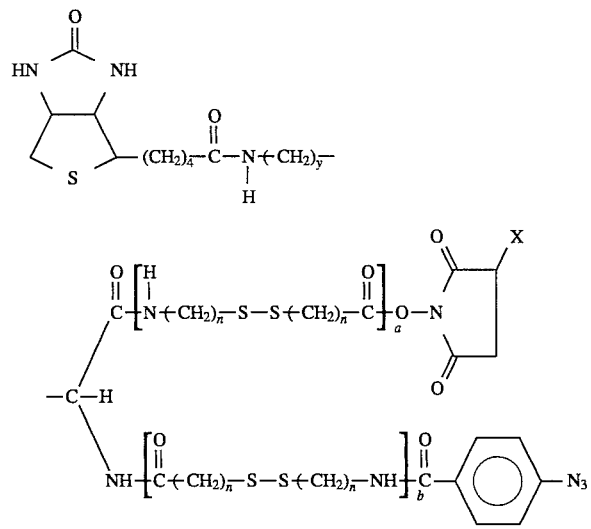

wherein a and b are zero or one, but are different, x is H or $SO_3Na$, n is an integer of 1 to 10, each n being the same or different and y is an integer of 1 to 10.

2. A compound of claim 1 wherein a is one and b is zero.
3. A compound of claim 2 wherein x is $SO_3Na$.
4. A compound of claim 1 wherein a is zero and b is one.
5. A compound of claim 4 wherein x is $SO_3Na$.
6. A compound of claim 1 wherein n is 2.
7. A compound of claim 1 wherein y is 4.
8. A compound of claim 7 wherein n is 2.
9. A compound of claim 8 wherein a is one and b is zero.
10. A compound of claim 9 wherein x is $SO_3Na$.
11. A compound of claim 8 wherein a is zero and b is one.
12. A compound of claim 11 wherein x is $SO_3Na$.

* * * * *